US00PP09581P

United States Patent [19]

Meilland

[11] Patent Number: Plant 9,581

[45] Date of Patent: Jun. 18, 1996

[54] HYBRID TEA ROSE PLANT NAMED 'MEITANET'

[75] Inventor: Alain A. Meilland, Antibes, France

[73] Assignee: The Conard-Pyle Company, West Grove, Pa.

[21] Appl. No.: 400,229

[22] Filed: Mar. 7, 1995

[51] Int. Cl.[6] ..... A01H 5/00

[52] U.S. Cl. ..... Plt./15

[58] Field of Search ..... Plt./15, 24

[56] References Cited

U.S. PATENT DOCUMENTS

Plt. 4,044 4/1977 Kordes ..... Plt./24

*Primary Examiner*—Howard J. Locker

*Attorney, Agent, or Firm*—Burns, Doane, Swecker & Mathis

[57] ABSTRACT

A new and distinct variety of Hybrid Tea intermediate rose plant is provided which abundantly forms attractive lemon yellow blossoms. Such blossoms commonly open slowly, are long-lasting and tend to well retain their coloration upon the passage of time. The blossoms commonly are borne in a regular display on erect stems wherein the stems commonly are somewhat uniform in length. The plant is well-suited for cut flower production in the greenhouse, and exhibits good disease resistance.

1 Drawing Sheet

SUMMARY OF THE INVENTION

The new variety of Hybrid Tea intermediate rose plant was created by artificial pollination wherein two parents were crossed which previously had been studied in the hope that they would contribute the desired characteristics. The female parent (i.e., the seed parent) of the new variety was the Golden Times variety (U.S. Plant Pat. No. 4,044). The male parent (i.e., the pollen parent) was the product of the cross of the Meitaranja variety (non-patented in the United States) and the Golden Garnette variety (U.S. Plant Pat. No. 1,898). The parentage of the new variety can be summarized as follows:

GOLDEN TIMES×(MEITARANJA×GOLDEN GARNETE).

The seeds resulting from the above pollination were sown and small plants were obtained which were physically and biologically different from each other. Selective study resulted in the identification of a single plant of the new variety.

It was found that the new variety of Hybrid Tea intermediate rose plant of the present invention possesses the following combination of characteristics:

(a) forms in abundance long-lasting double Lemon Yellow blossoms on erect stems that well retain their coloration when cut and placed in a vase, and (b) also is well suited for cut flower production under greenhouse conditions.

The Hybrid Tea intermediate classification designates that the new variety exhibits somewhat shorter stems than a typical Hybrid Tea rose variety.

The blossoms of the new variety commonly are borne on very erect stems that tend to be somewhat regular in length. Also, the blossoms tend to open slowly, tend to retain a substantially constant coloration with the passage of time, and tend to be very long-lasting when cut and placed in a vase.

The new variety has been found to undergo asexual propagation in France by a number of routes, including budding, grafting, and cuttage. The characteristics of the new variety have been found by such methods in France to be stable and to be strictly transmissible from one generation to another.

The new variety has been named the Meitanet variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Le Cannet des Maures, Var, France.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface;

FIG. 15 — illustrates a specimen of a leaf with five leaflets — plan view — under surface; and FIG. 16 — illustrates a specimen of a leaf with seven leaflets — plan view — upper surface.

DETAILED DESCRIPTION

Figures 1, 2, 3, 4, 5, 6, 7, 8, 9, 10, 11, 12, 13, 14, 15, 16:
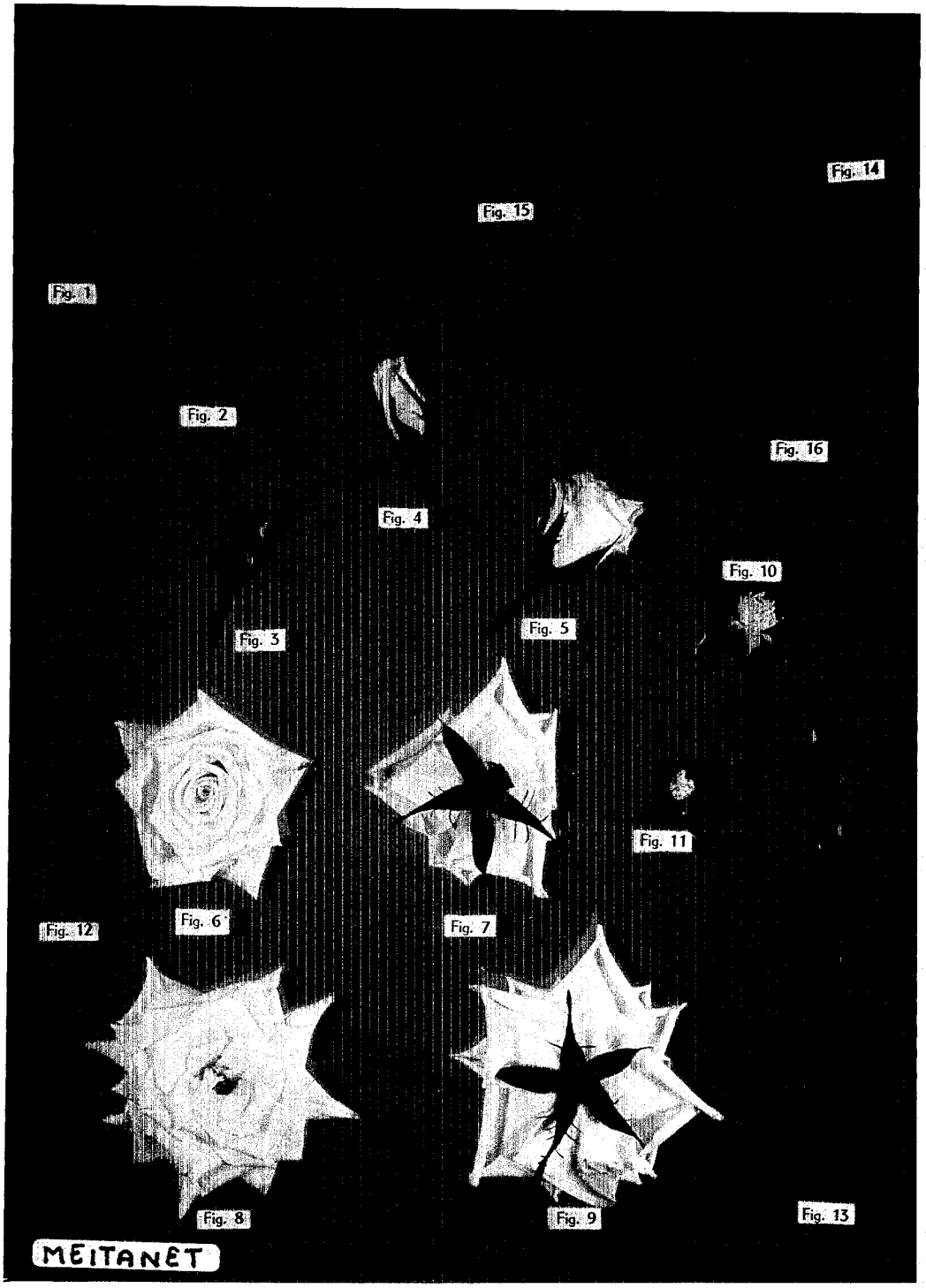

The chart used in the identification of the colors is that of The Royal Horticultural Society (R.H.S. Colour Chart). The description is based on the observation of three year-old plants while budded on *Rosa indica* understock and growing during June in greenhouses at Le Cannet des Maures, Var, France. The coloration in common terms precedes reference to the chart.

Class: Hybrid Tea intermediate.

Plant:

*Height.*—When pruned to a height of 85 cm. the floral stems commonly are approximately 40 to 50 cm. in length.

*Habit.*—Erect.

Branches:

*Color.*—Young stems: medium green, Green Group 136B. Adult wood: medium green, Green Group 136A and 136B.

*Thorns.*—Size: small to medium. Quantity: many. Color: greenish on young stems and light brown on adult wood.

Leaves:

Stipules.—Adnate, pectinate, very large and linear.

*Petioles.*—Upper surface: striped reddish brown on young foliage, and medium green on adult foliage with glandular edges. Under surface: light green and bear some small prickles.

*Leaflets.*—Number: 3, 5, and 7 (most often). Shape: oval. Serration: single and regular. Texture: very consistent. General appearance: dense, dark and bright glossy foliage. Color (young foliage): upper surface: dark medium green, Green Group 136B, and more or less stained and edged reddish brown. under surface: dark medium green, Green Group 136B, and more or less stained and edged reddish brown. Color (adult foliage): upper surface: dark green, Green Group 139A. under surface: medium green, Green Group 136B.

Inflorescence:

*Number of flowers.*—Usually one flower per stem. The flower productivity commonly is approximately 200 to 250 flowers/m.$^2$ per year when grown under greenhouse conditions at a rate of 6½ to 7 plants/m.$^2$.

*Peduncle.*—Medium green in coloration, and approximately 6 cm. in length on average.

*Sepals.*—Upper surface: tomentose, and greenish in coloration. Under surface: light green, and the sepals commonly have extensions at the edges (as illustrated).

*Buds.*—Shape: conical. Length: approximately 3 cm. on average. Size: medium. Color upon opening: Upper surface: Lemon Yellow, Yellow Group 12A. Under surface: Lemon Yellow, Yellow Group 13C.

*Flower.*—Shape: cup-shaped and double. Diameter: approximately 9 to 10 cm. on average. Color (when opening begins): upper surface: Lemon Yellow, Yellow Group 12A, to Mimosa Yellow, Yellow Group 8D on the petal edges, and commonly with whitening on the outer petals. Such whitening approaches White Group 155A. Under surface: Lemon Yellow, Yellow Group 12A, to Mimosa Yellow, Yellow Group 8D on the petal edges and commonly with whitening on the outer petals. Such whitening approaches White Group 155A. Color (when blooming): upper surface: Lemon Yellow, Yellow Group 12A, to Mimosa Yellow, Yellow Group 8D on the petal edges and commonly with whitening on the outer petals. Such whitening approaches White Group 155A. Under surface: Lemon Yellow, Yellow Group 12A, to Mimosa Yellow, Yellow Group 8D on the petal edges and commonly with whitening on the outer petals. Such whitening approaches White Group 155A. Color (at end of opening): upper surface: Lemon Yellow, Yellow Group 12A, to Mimosa Yellow, Yellow Group 8D on the petal edges and commonly with whitening on the outer petals. Such whitening approaches White Group 155A. Under surface: Lemon Yellow, Yellow Group 12A, to Mimosa Yellow, Yellow Group 8D on the petal edges and commonly with whitening on the outer petals. Such whitening approaches White Group 155A. Fragrance: slight anise. Lasting quality: very long when cut and placed in a vase. Blossoms commonly last approximately 12 days when cut and placed in a vase and longer on the plant. Petal form: rounded with reflexed edges. Petal drop: good. Stamen number: approximately 183 on average. Petal number: approximately 33 on average. Anthers: normal, golden yellow in coloration. Filaments: bright yellow in coloration, and commonly of irregular heights. Pistils: approximately 76 on average. Stigmas: normal, greenish strawlike. Styles: greenish strawlike. receptacle: medium green, tomentose, and in longitudinal section in the shape of a funnel. Hips and seeds: are formed.

Development:

*Vegetation.*—Strong.

*Blooming.*—Abundant.

*Resistance to disease.*—*Good.*

I claim:

1. A new and distinct variety of Hybrid Tea intermediate rose plant characterized by the following combination of characteristics:

(a) forms in abundance long-lasting double lemon yellow blossoms on erect stems that well retain their coloration when cut and placed in a vase, and (b) also is well suited for cut flower production under greenhouse conditions substantially as herein shown and described.

* * * * *

MEITANET